United States Patent
Friedman et al.

(10) Patent No.: US 6,753,783 B2
(45) Date of Patent: Jun. 22, 2004

(54) PATIENT POSITIONING MONITORING APPARATUS AND METHOD OF USE THEREOF

(75) Inventors: Mark B. Friedman, Pittsburgh, PA (US); Randall W. Casciola, Pittsburgh, PA (US)

(73) Assignee: AugmenTech, Inc., Pittsburgh, PA (US)

( * ) Notice: Subject to any disclaimer, the term of this patent is extended or adjusted under 35 U.S.C. 154(b) by 120 days.

(21) Appl. No.: 10/113,422

(22) Filed: Apr. 1, 2002

(65) Prior Publication Data

US 2002/0145526 A1 Oct. 10, 2002

Related U.S. Application Data

(60) Provisional application No. 60/280,274, filed on Mar. 30, 2001.

(51) Int. Cl.[7] .................. G08B 23/00; G08B 13/14; A61B 5/103; G01B 7/14
(52) U.S. Cl. ..................... 340/573.7; 340/573.1; 340/572.1; 340/572.5; 600/595; 324/207.11
(58) Field of Search ................. 340/573.7, 572.4, 340/572.5, 572.1, 573.1, 825.49; 600/595; 324/207.11–207.25

(56) References Cited

U.S. PATENT DOCUMENTS

| | | | |
|---|---|---|---|
| 3,810,147 A | | 5/1974 | Lichtblau .................... 340/280 |
| 3,967,161 A | | 6/1976 | Lichtblau ................ 317/101 R |
| 5,570,082 A | | 10/1996 | Mahgerefteh et al. ...... 340/604 |
| 5,592,401 A | * | 1/1997 | Kramer ..................... 702/153 |
| 5,729,129 A | * | 3/1998 | Acker .................. 324/207.12 |
| 5,804,810 A | * | 9/1998 | Woolley et al. ............. 235/492 |
| 5,838,233 A | * | 11/1998 | Hawes et al. ............ 340/572.5 |
| 5,914,660 A | * | 6/1999 | Mesibov et al. ......... 340/573.7 |
| 5,941,836 A | | 8/1999 | Friedman .................... 600/595 |
| 5,963,134 A | | 10/1999 | Bowers et al. ........... 340/572.1 |
| 6,043,746 A | | 3/2000 | Sorrells ................... 340/572.7 |
| 6,160,478 A | * | 12/2000 | Jacobsen et al. ....... 340/539.12 |
| 6,182,352 B1 | | 2/2001 | Deschenes et al. ........ 29/602.1 |
| 6,204,765 B1 | * | 3/2001 | Brady et al. ............. 340/572.1 |
| 6,249,229 B1 | | 6/2001 | Eckstein et al. ......... 340/572.4 |
| 6,417,771 B1 | * | 7/2002 | Tyren ..................... 340/572.2 |
| 6,480,111 B2 | * | 11/2002 | Canady et al. ........... 340/573.1 |
| 2001/0040507 A1 | | 11/2001 | Eckstein et al. |
| 2002/0183657 A1 | * | 12/2002 | Socci et al. ................. 600/595 |

\* cited by examiner

Primary Examiner—Jeffery Hofsass
Assistant Examiner—Anne V. Lai
(74) Attorney, Agent, or Firm—Webb Ziesenheim Logsdon Orkin & Hanson P.C.

(57) ABSTRACT

A patient position monitoring apparatus and method includes an article configured to be worn by a patient. The article includes a plurality of resonators with each resonator responsive to a wireless excitation signal for causing the unique change in the excitation signal or for outputting a unique wireless response signal. The resonators are stimulated with a first wireless excitation signal when the article is being worn by a patient. The unique change in the excitation signal and /or the unique response signal of each resonator responding to the first excitation signal is determined. From the thus detected response, a signal strength of the unique change in the excitation signal and/or the unique response signal for each responding resonator is determined. From the thus determined signal strengths, the relative locations of the responding resonators with respect to each other can be determined.

17 Claims, 9 Drawing Sheets

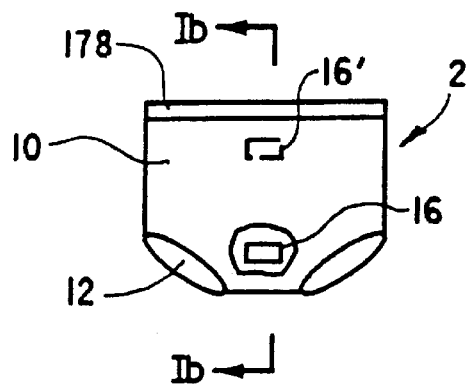
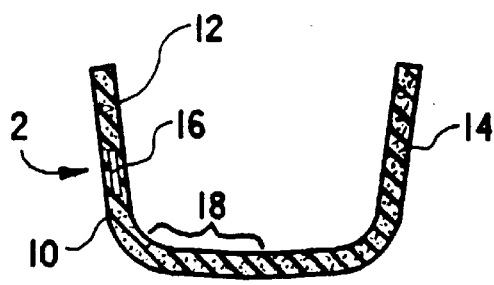
FIG. 1a  FIG. 1b
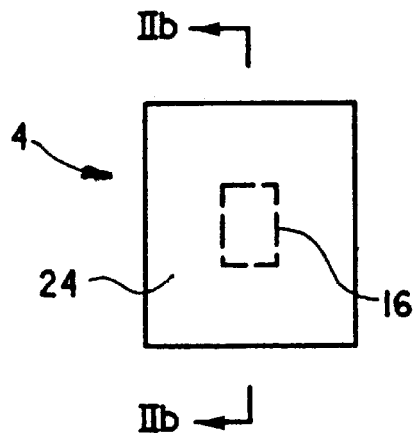
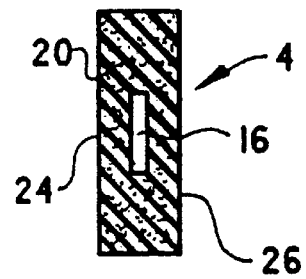
FIG. 2a  FIG. 2b
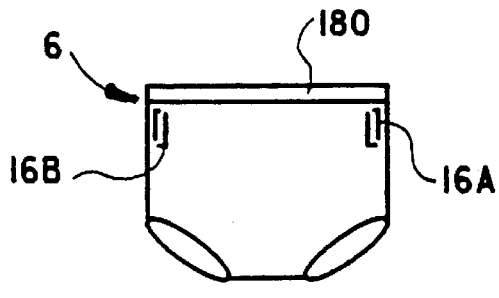
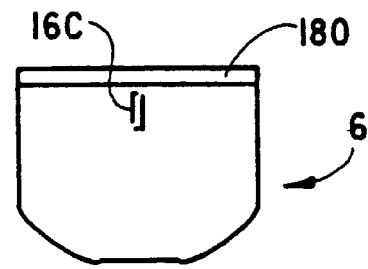
FRONT  BACK
FIG. 3a  FIG. 3b

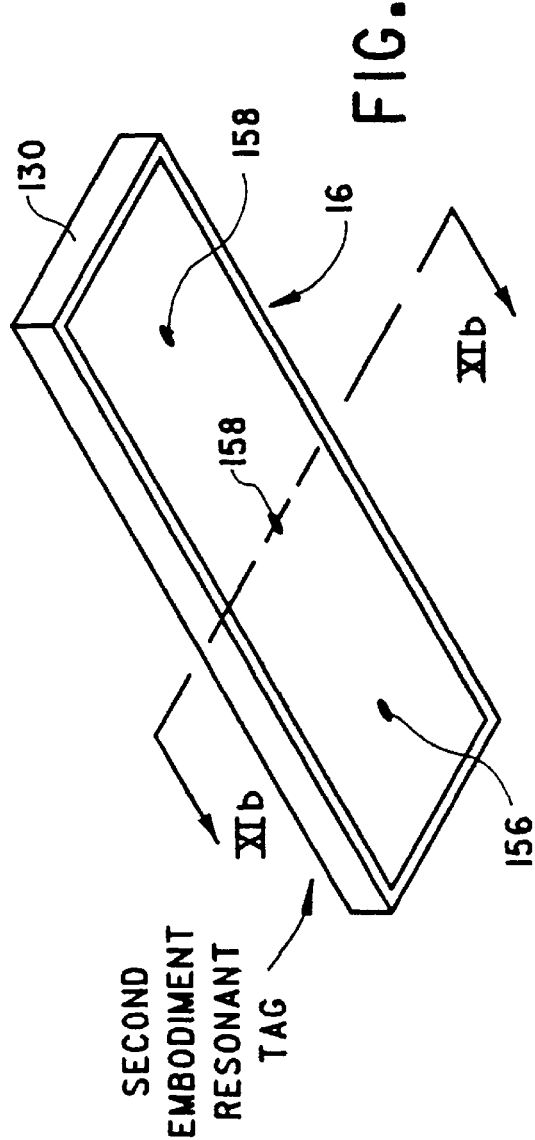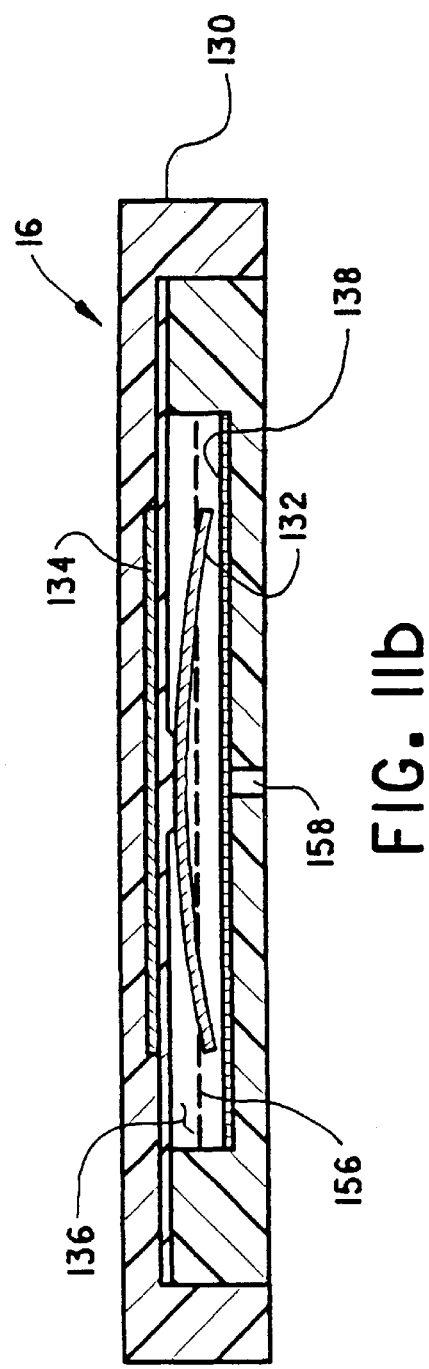

PATIENT POSITIONING MONITORING APPARATUS AND METHOD OF USE THEREOF

CROSS REFERENCE TO RELATED APPLICATION

This application claims priority from U.S. Provisional Patent Application Serial No. 60/280,274, filed Mar. 30, 2001.

BACKGROUND OF THE INVENTION

1. Field of the Invention

The present invention relates to incontinence monitoring and/or position monitoring of patients.

2. Description of Related Art

Incontinence is universal among the very young and increasingly common among the very old. Incontinence may also be a consequence of surgical procedures or neurological impairments. There is a need to determine when an absorbent product, e.g., a diaper or bed pad, for a patient who is incontinent is wet, without disturbing the patient.

A wide variety of means have been devised to detect when a diaper is wet without removing the diaper. These include visual indicators and electronic wetness detection systems. Visible indicators for disposable diapers typically are chemicals within the deep layers of the diaper, adjacent to a translucent moisture impermeable outer layer, that change color when wet. For a caregiver to see that the diaper is wet and needs to be changed, the indicator region of the diaper must be visible. This requires undressing the wearer of the diaper when the user is dressed, and pulling back blankets, sheets and bed clothes when the wearer is in bed. It also may require rolling a wearer over to view the rear of the diaper if the wearer is asleep on their back. The process of obtaining a view of chemical wetness indictors is clearly disruptive of the wearers activities. It may be particularly disruptive when checking for wetness awakes a sleeper whether or not their diaper is actually wet and in need of changing. The chief virtue of visible wetness indicators is that they are inexpensive to produce.

Various electronic diaper wetness detection indication systems have been developed specifically to provide remote sensing of when a diaper needs to be changed. These typically involve at least two components attached to the diaper. Systems dependent on radio transmitters also require a remote radio receiver. Electronic wetness detection systems usually have an inexpensive disposable sensor within the diaper and a reusable alarm or transmitter attached to the outside of the diaper that is connected to the wetness sensor within. Typically, the sensing element includes two or more conducting elements separated by a wetable membrane that insulates between the conductors when dry and conducts electricity or otherwise changes impedance between the sensor when wet with urine or other electrolyte solutions. The electrical power that activates the external signaling circuit may be sourced from a battery in the attached electronics package or by galvanic reaction between metallic electrodes in the diaper.

For audio alarms, the detachable reusable electronic package produces an audible signal to alert the caregiver when urine is sensed within the diaper. For radio frequency (RF) alerting systems, a radio transmission is made by the reusable external transmitter when urine is sensed within the diaper. This RF transmission is received by a remote device that is configured to alert a caregiver that the diaper is wet. Audible electronic systems have the disadvantage of requiring the caregiver to be within hearing range at the time the audible alert is generated. Furthermore, sound generated can be disruptive of ongoing activities, such as sleep or social interaction, particularly for incontinent adults. Radio alerting systems can be more private in signaling the need to change a wet diaper or incontinence bed pad.

While the electronic systems described above have the advantage of not requiring a caregiver to physically disturb the wearer of the diaper in order to determine if the diaper is wet, the reusable electronics package attached to the diaper may be uncomfortably large and must be recovered after each diaper change for reattachment to a fresh diaper. The need to recover and reuse a relatively expensive electronics package attached to a soiled diaper every time the diaper is changed is onerous, especially when the diaper is soiled with feces. Experience shows that the detachable electronics packages are often misplaced or lost in institutional settings when diapers are removed because wearers are being bathed or changed or having a medical procedure.

All previous electronic wetness sensors for incontinence products require two or more sensing elements separated by an insulating region, attached to the electronic sensing circuit. Usually, these sense wetness by the increased conductance between two electrodes, but changing capacitance has also been used to detect wetness. A problem with the prior art incontinence detecting systems is that they require the attachment of a powered audible or radio-signaling device to the diaper and that they require sensing electrodes to function.

It is, therefore, an object of the present invention to overcome the above problems and others by providing a system and method of use thereof for remotely detecting when a diaper is wet without the need to attach a powered signaling device to the diaper. It is an object of the present invention to provide a system and method of use thereof for remotely detecting the position of a patient. Still further objects will become apparent to those of ordinary skill in the art upon reading and understanding the following detailed description.

SUMMARY OF THE INVENTION

Accordingly, I have invented a patient monitoring system that includes a plurality of resonators, each responsive to at least one wireless excitation signal for causing a unique change in the excitation signal and/or outputting a unique wireless response signal. The system also includes an article configured to be worn by a patient. The article includes the plurality of resonators received at predetermined locations thereon. The article is configured to avoid movement of each resonator relative to a body of the patient when it is being worn. A transceiver supplies a first excitation signal, detects for each resonator responding to the first excitation signal a strength of the unique change in the first excitation signal and/or a strength of the unique response signal and determines therefrom a first relative position of each responding resonator with respect to each other.

The transceiver can also supply a second excitation signal, detect for each resonator responding to the second excitation signal a strength of the unique change in the second excitation signal and a strength of the unique response signal and determines therefrom a second relative position of each responding resonator with respect to each other.

The system can also include a detector responsive to a change in the first and second relative positions of one or more responding resonators for generating an indication related to a change in position of the patient between the first and second excitation signals, or a lack change in the first and second relative positions of one or more responding resonators for generating an indication related to an absence of a change in position of the patient between the first and second excitation signals.

The transceiver can include at least one antenna position adjacent a patient receiving surface for transmitting excitation signals. The system can further include a detector responsive to interaction between the at least one antenna at each resonator responding to each excitation signal for detecting the strength of the unique change in the excitation signal caused by each resonator. The patient receiving surface can be a surface of a mattress or a surface of a chair.

The transceiver can also include at least one antenna positioned adjacent the patient receiving surface for transmitting excitation signals and for receiving after each excitation signal is terminated the unique response signal output by each resonator responding thereto. The detector can be coupled to the at least one antenna for detecting the strength of each unique response signal received thereby.

The transceiver can also include at least one first antenna positioned adjacent the patient receiving surface for transmitting each excitation signal and the detector can be responsive to interaction between at least one second antenna and each resonator responding to each excitation signal during transmission thereof for detecting the strength of the unique change in the excitation signal caused by each resonator.

The transceiver can also include a plurality of antennas each positioned at a unique location adjacent the patient receiving surface, with each antenna individually selectable for transmitting at least one excitation signal. The detector can be selectively coupled to each antenna for receiving therefrom the unique change in the excitation signal caused by each resonator responding to the excitation signal.

The unique change in the first excitation signal can include energy absorption in one or more frequencies of the excitation signal. The unique response signal of each resonator can include a unique frequency.

I have also invented a patient position monitoring method that includes providing an article configured to be worn by a patient. The article includes a plurality of resonators affixed thereto. Each resonator is responsive to a wireless excitation signal for causing a unique change in the excitation signal and/or outputting a unique wireless response signal. The resonators are stimulated with a first wireless excitation signal when the article is being worn by a patient. For each resonator responding to the first excitation signal, the unique change in the excitation signal and/or the unique response signal is detected. For each resonator responding to the first excitation signal a signal strength of the unique change in the excitation signal and/or the unique response signal is determined. From these signal strengths, the relative locations of the resonators responding to the first excitation signal with respect to each other is determined.

The method can also include stimulating the resonators with a second wireless excitation signal and detecting for each resonator responding to the second excitation signal, the unique change in the excitation signal and/or the unique response signal. For each resonator responding to the second excitation signal, a signal strength of the unique change in the excitation signal and/or the unique response signal is determined. From the thus determined signal strengths, the relative locations of the resonators responding to the second excitation signal with respect to each is determined.

Lastly, I have invented a patient orientation monitoring system that includes an article configured to be worn by a patient and a plurality of resonators supported by the article, with each resonator responsive to a wireless excitation signal for causing a unique change in the excitation signal and/or outputting a unique wireless response signal. The system can also include means for outputting a first wireless excitation signal when the article is being worn by the patient and for receiving from each resonator responding to the first excitation signal the unique change in the excitation signal and/or the unique response signal therefor. A determining means can determine therefrom first relative positions of the responding resonators with respect to each other.

The determining means can include a detector programmed to determine from the first relative positions of the responding resonators with respect to each other an orientation of the patient.

The means for outputting and receiving can also output a second wireless excitation signal and can receive from each resonator responding to the second excitation signal the unique change in the excitation signal and the unique response signal. The determining means can determine therefrom second relative positions of the responding resonators with respect to each other. The determining means can include a detector programmed to determine from the first and second relative positions of the responding resonators with respect to each other whether the patient has changed orientation.

The means for outputting and receiving can include at least one antenna positioned adjacent a patient receiving surface for transmitting each excitation signal and for receiving from each resonator responding to the excitation signal the unique change in the excitation signal and/or the unique response signal. A determining means can include a detector responsive to each antenna for receiving therefrom for each resonator responding to the excitation signal the unique change in the excitation signal and/or the unique response signal.

BRIEF DESCRIPTION OF THE DRAWINGS

FIG. 1a is a front view of a disposable diaper including a resonant tag therein;

FIG. 1b is a section taken along lines Ib—Ib in FIG. 1a;

FIG. 2a is a top view of a pad including a resonant tag;

FIG. 2b is a section taken along lines IIb—IIb in FIG. 2a;

FIGS. 3a and 3b are front and back views of an undergarment including resonant tags affixed thereto;

FIG. 11a is a perspective view of a second embodiment resonant tag;

FIG. 11b is a section taken along lines XIb—XIb in FIG. 11a;

DETAILED DESCRIPTION OF THE INVENTION

Figure 4A:
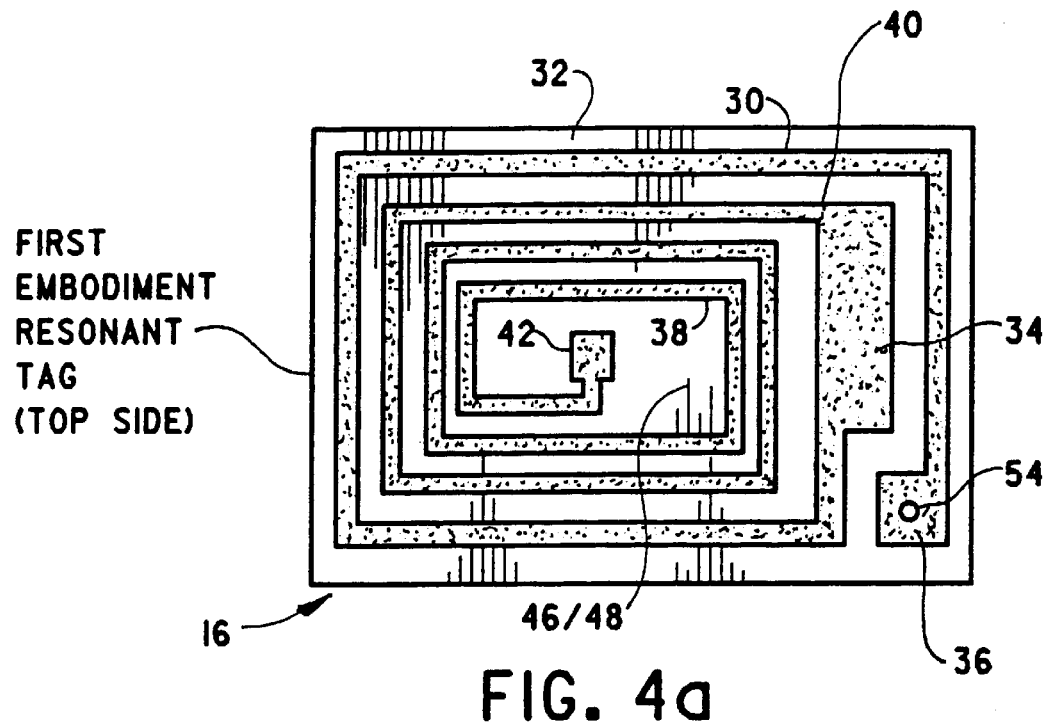
FIGS. 4a and 4b are topside and bottom side views of a first embodiment resonant tag.

The present invention will be described with reference to the accompanying FIGS. where like reference numbers correspond to like elements.

The present invention is directed to remote patient incontinence monitoring and/or remote patient position monitoring. In connection with patient incontinence monitoring, an article configured to receive fluid discharged from a patient is provided. The article can be a disposable diaper 2, shown in FIGS. 1a and 1b, and/or a disposable pad 4, shown in FIGS. 2a and 2b, or any other article that is suitable for receiving fluid discharged by a patient. In connection with patient positioning monitoring, the article can be diaper 2 or underwear or undergarment 6, as shown in FIGS. 3a and 3b, or any other article that can be worn by a patient without substantial movement of the article with respect to the patient. In the following discussion, use of the invention for patient incontinence monitoring will be first described followed by use of the invention for patient position monitoring.

With reference to FIGS. 1a and 1b, disposable diaper 2 includes an outer, fluid impermeable cover 10, an inner lining 12 and liquid absorbent material 14 therebetween. An RF tag 16 is received between outer cover 10 and inner lining 12 with one or more circuit elements (described hereinafter) of RF tag 16 in contact with or in space relation with absorbent material 14. One or more other RF tags 16' can also be positioned between outer cover 10 and inner lining 12 at a different locations in diaper 2. When two or more RF tags 16, 16' are provided, each RF tag 16, 16' has a uniquely detectable response to a wireless excitation signal.

Inner lining 12 can be fluid permeable or can include a fluid permeable part 18 arranged so that when diaper 2 is worn by a patient, fluid permeable part 18 is positioned to receive fluid discharged from the urine discharge orifice and/or the fecal discharge orifice of the patient.

With reference to FIGS. 2a and 2b, disposable pad 4 can be an incontinence pad, a gauze or pad configured for application to bleeding or oozing wounds of a patient or the sterile pad of a bandage. Disposable pad 4 includes liquid absorbent material 20 received in a casing 22 having a fluid impermeable side 24 and a fluid permeable side 26. RF tag 16 is received in casing 22 in contact with or in spaced relation with absorbent material 20. In use, pad 4 is positioned with fluid permeable side 26 positioned to receive fluid discharged from the patient.

Embodiments of RF tag 16 suitable for use in remote incontinence monitoring and/or remote position monitoring are found in the art of electronic article surveillance (EAS). A nonlimiting example of a first embodiment RF tag 16 and method of use thereof are disclosed in U.S. Pat. Nos. 3,810,147 and 3,967,161 which are incorporated herein by reference.

Figure 4B:
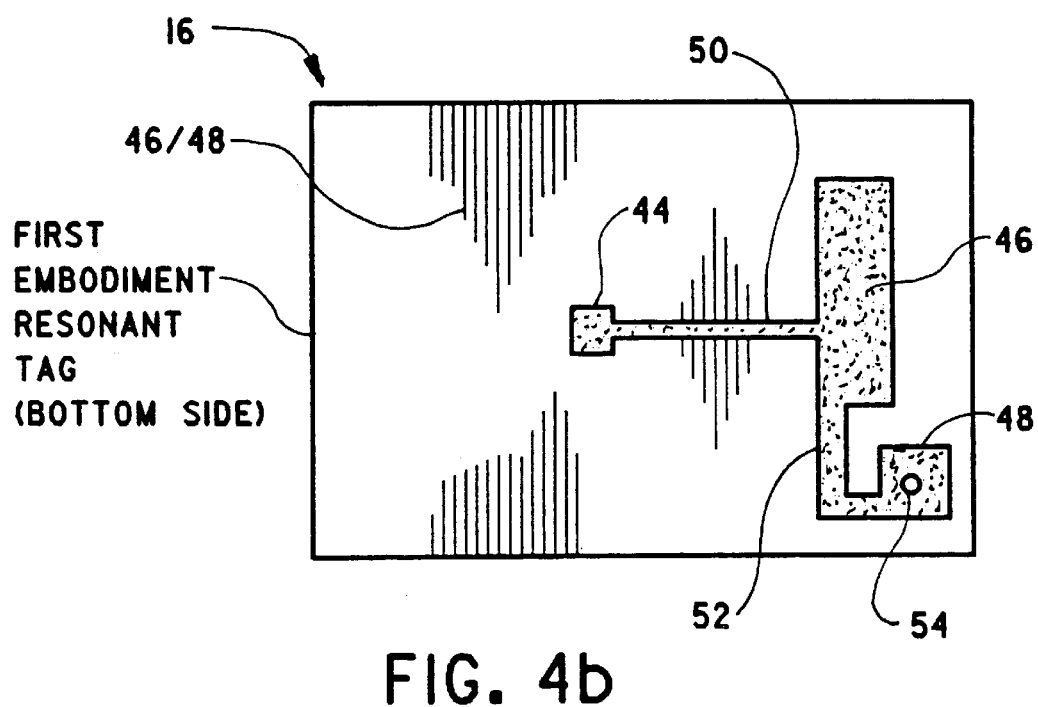

With reference to FIGS. 4a and 4b, one exemplary instantiation of the first embodiment RF tag 16 includes a first conductive path 30 arranged in a generally rectangular pattern on a top surface of a flexible insulating substrate 32 and terminating at one end in a conductive area 34 disposed in spaced relation near one edge of substrate 32. The other end of path 30 terminates at a conductive area 36 disposed near one corner of substrate 32. A second conductive path 38 is formed as a rectangular spiral on substrate 32 and terminates at its outer end at a junction 40 with area 34, and at its inner end at a conductive area 42 centrally of the spiral.

The bottom surface of substrate 32 includes a conductive area 44 in alignment and generally coextensive with conductive area 42. A pair of conductive areas 46 and 48 are positioned in alignment and generally coextensive with areas 34 and 36. Conductive areas 44 and 46 are interconnected by a conductive path 50, while conductive areas 46 and 48 are interconnected by a conductive path 52. An electrical connection 54 is made between areas 36 and 48 by means of a conductive pin or the like extending through substrate 32.

Figure 5:
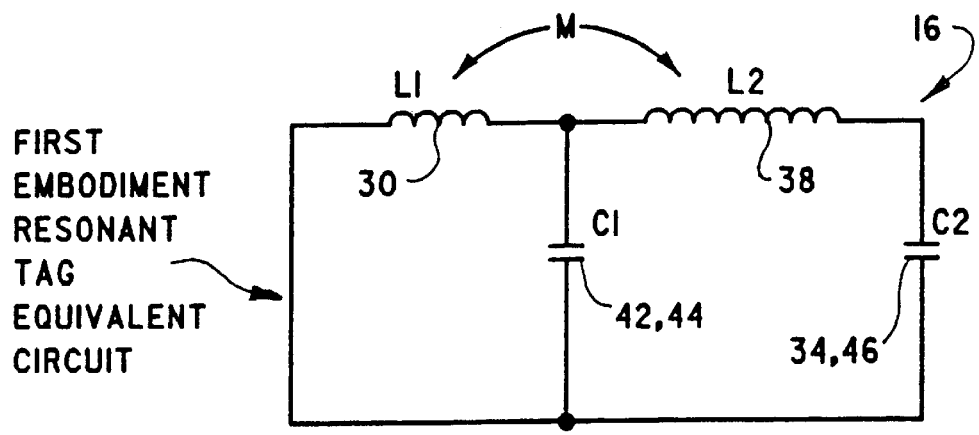
FIG. 5 is an equivalent electrical circuit diagram of the resonant tag shown in FIGS. 4a and 4b.

With reference to FIG. 5 and with continuing reference to FIGS. 4a and 4b, conductive paths 30 and 38 define inductors L1 and L2 which act as an antenna of RF tag 16. Conductive areas 42 and 44 spaced by substrate 32 define a first capacitor C1, while conductive areas 34 and 46 spaced by substrate 32 define a second capacitor C2. While the first embodiment RF tag 16 includes two inductors L1 and L2 and two capacitors C1 and C2, this first embodiment RF tag 16 can be modified so that it only includes one inductor L and one capacitor C. The first embodiment RF tag 16 shown in FIGS. 4a and 4b is strictly for the propose of illustration and is not to be construed as limiting the invention.

The first embodiment RF tag 16 can be utilized with remote excitation and detection circuitry in essentially two modes of operation. Namely, an energy absorption mode and an energy radiation mode. Use of the first embodiment RF tag 16 in the energy absorption mode will now be described with reference to FIGS. 6–9.

Figure 6:
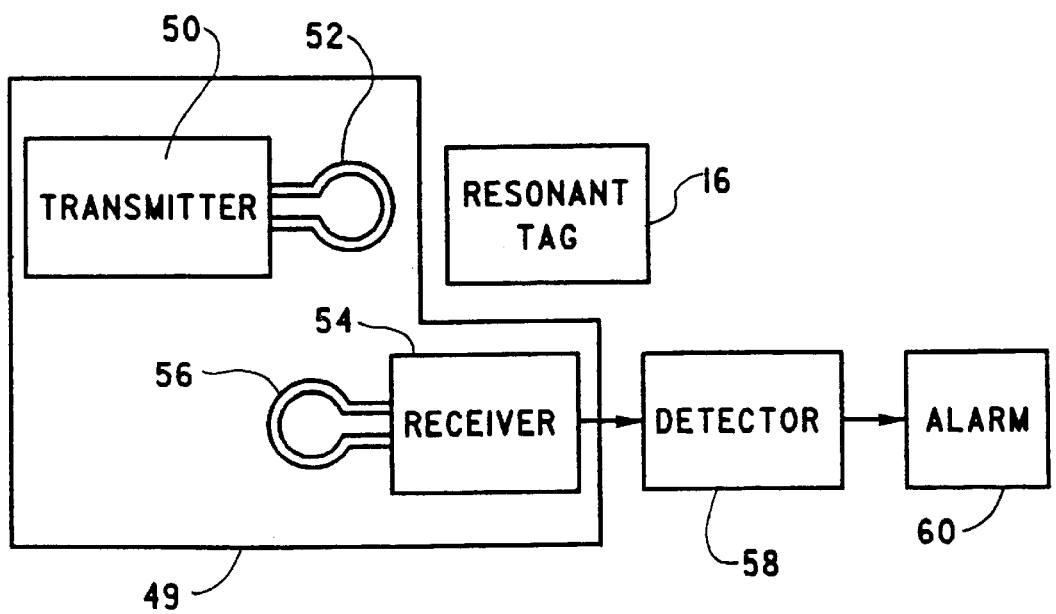
FIGS. 6–10 are schematic drawings of different embodiments of circuits that can be utilized for exciting the first embodiment resonant tag shown in FIGS. 4a and 4b with an excitation signal and for detecting the response of the resonant tag to the excitation signal.

With reference to FIG. 6, a first circuit for use with the first embodiment RF tag 16 in the energy absorption mode includes a first transceiver 49 for exciting RF tag 16 with a wireless excitation signal and for detecting the response of RF tag 16 to the excitation signal. Transceiver 49 includes a transmitter 50 coupled to an antenna 52 for exciting RF tag 16 with the wireless excitation signal and a receiver 54 coupled to an antenna 56 for wirelessly detecting the response of RF tag 16 to the excitation signal.

In the absence of RF tag 16 in the area between antennas 52 and 56, the excitation signal provided by antenna 52 is sensed by antenna 56 without interference from RF tag 16. However, when RF tag 16 is present between antennas 52 and 56, RF tag 16 couples to the excitation signal provided by antenna 52 when the frequency of the excitation signal is the same as the resonant frequency of RF tag 16. In response to RF tag 16 absorbing energy from the excitation signal, antenna 56 detects a reduction in the signal strength of the excitation signal at the resonant frequency of RF tag 16. In EAS applications, this reduction in the signal strength can be sensed by a detector 58 which is programmed to activate an alarm 60 in response.

Figure 7:
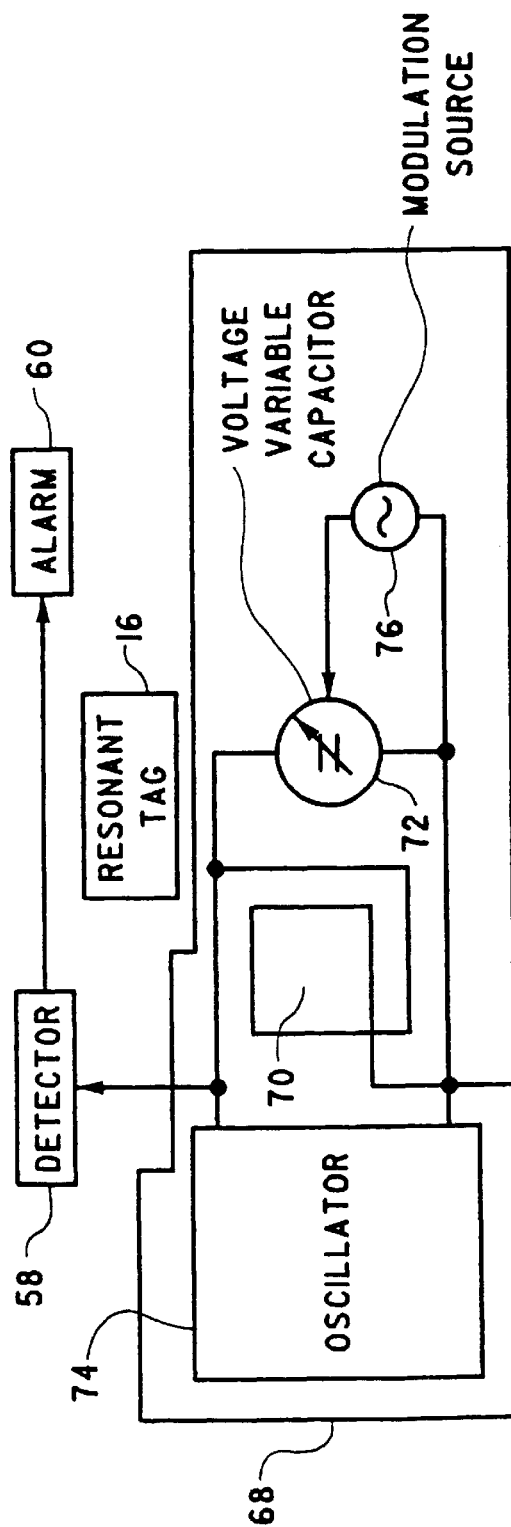

With reference to FIG. 7, a second circuit for use with the first embodiment RF tag 16 in the energy absorption mode includes a transceiver 68 having an antenna loop 70 resonant with a voltage variable capacitor 72 which is driven by an oscillator 74. A modulating signal is provided by a modulation source 76 coupled to a control input of capacitor 72 to vary the capacitance thereof and thus the resonance of the tuned circuit. In operation, when RF tag 16 is coupled with antenna 70, the antenna loop 70 becomes loaded with the reflected impedance of RF tag 16 which produces a change in the voltage across the antenna loop 70. This change can be sensed by detector 58 which activates alarm 60 in response.

Figure 8:
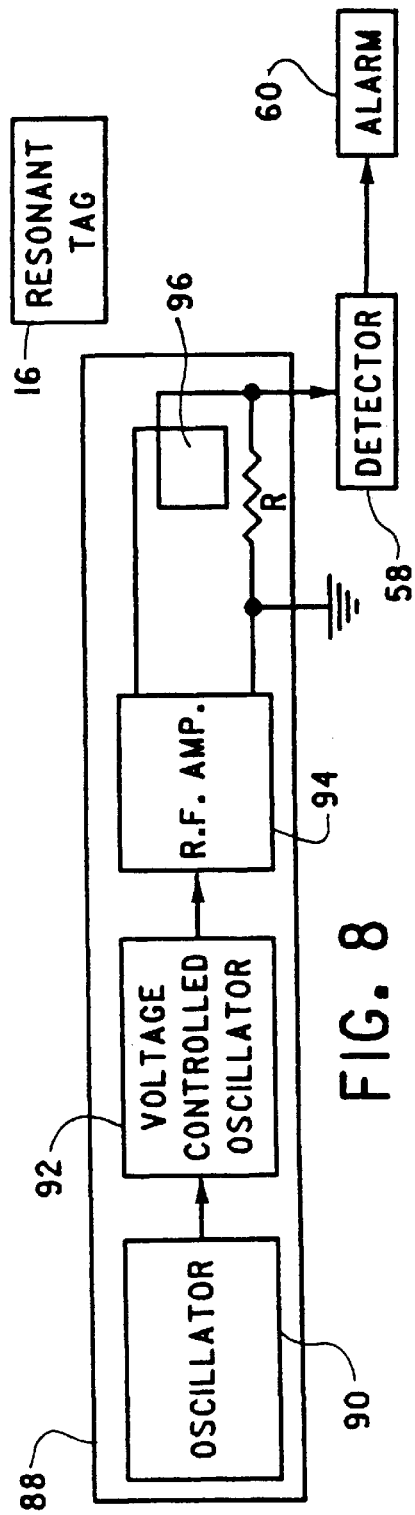

With reference to FIG. 8, a third circuit for use with the first embodiment RF tag 16 in the energy absorption mode includes a transceiver 88 which includes an oscillator 90 which drives a voltage controlled oscillator 92 which, in turn, drives an RF amplifier 94 which energizes a non-resonant loop antenna 96. When RF tag 16 is coupled to antenna 96, the impedance of RF tag 16 is reflected into antenna 96 thereby causing a change in the apparent resistance of antenna 96. This change can be sensed across a resistor R by detector 58 which activates alarm 60 in response.

Figure 9:
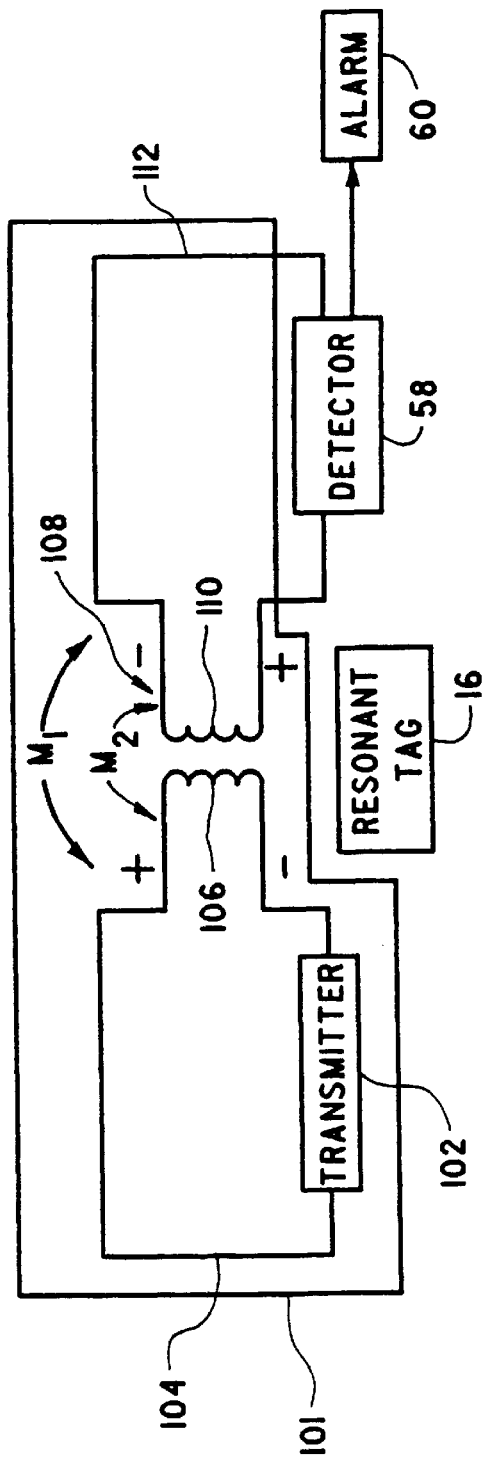

With reference to FIG. 9, a fourth circuit for use with the first embodiment RF tag 16 in the energy absorption mode includes a transceiver 101 having a transmitter 102 coupled to an antenna loop 104 in series with one winding 106 of a transformer 108. Transformer 108 includes another winding 110 in series with an antenna loop 112 of a receiving antenna to which detector 58 is coupled. Transformer 108 has variable mutual coupling $M_2$ that it is adjusted in response to RF tag 16 moving into mutually coupling relationship with antenna loops 104 and 112. In response to a change in the mutual coupling, detector 58 detects a corresponding change in a current flowing in antenna loop 112. This change can be sensed by detector 58 which activates alarm 60 in response.

Next, the use of the first embodiment RF tag 16 in the energy radiation mode will be described with reference to FIGS. 10 and 6.

Figure 10:
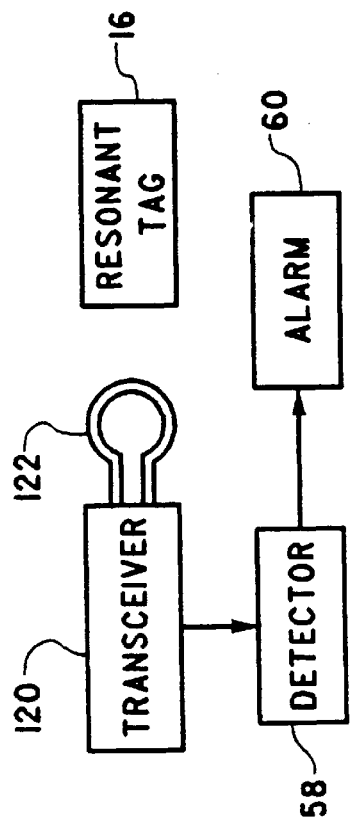

With reference to FIG. 10, a circuit for use with the first embodiment RF tag 16 in the energy radiation mode includes a transceiver 120 which outputs an excitation signal via an antenna 122. In response to RF tag 16 receiving this excitation signal RF tag 16 commences oscillating at its resonant frequency. At a suitable time, transceiver 120 terminates the excitation signal whereupon energy stored in RF tag 16 causes RF tag 16 to continue oscillating at its resonant frequency, thereby generating a wireless response signal, for a brief interval after termination of the excitation signal. During this brief interval, transceiver 120 detects the wireless response signal output by RF tag 16 via antenna 122. In response to detecting the wireless response signal, detector 58 activates alarm 60.

As an alternative to utilizing transceiver 120 to detect the wireless response signal, transceiver 49, shown in FIG. 6, having transmitter 50 and receiver 54 coupled to antennas 52 and 56, respectively, can be utilized to output the excitation signal and receive the wireless response signal output by RF tag 16.

The detection of a wireless response signal output by an RF tag 16 after termination of an excitation signal utilized to excite the RF tag 16 to resonance is disclosed in U.S. patent application Publication No. 2001/0040507 to Eckstein et al.

With reference to FIGS. 11a and 11b, a second embodiment RF tag 16 utilized in an energy radiation mode of operation includes a housing 130 which supports a magnetostrictive element 132 in the magnetic field of a magnet 134. More specifically, magnetostrictive element 132 is suspended in a cavity 136 of housing 130 in a manner whereupon magnetostrictive element 132 is biased by the magnetic field of magnet 134. Also received in cavity 136 is a liquid absorbent material 138. In the absence of discharged fluid, liquid absorbent material 138 is spaced from magnetostrictive element 132.

Figure 12:
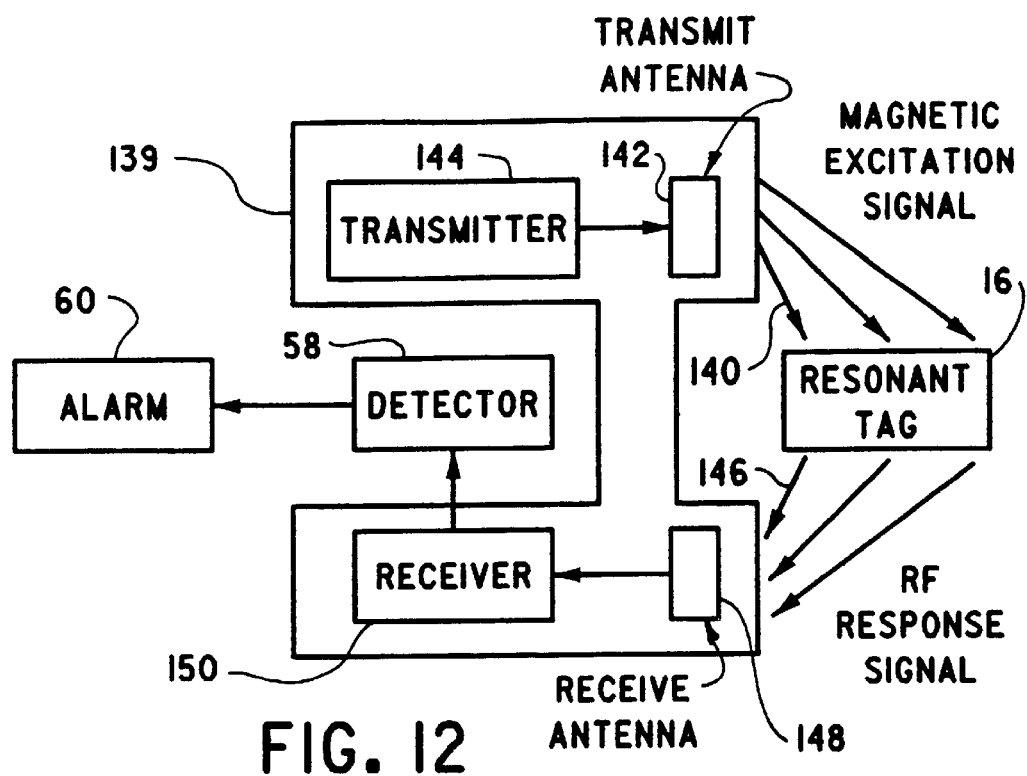
FIG. 12 is a schematic drawing of a circuit for exciting the second embodiment resonant tag shown in FIGS. 11a and 11b with an excitation signal and for detecting the response of the resonant tag to the excitation signal.

With reference to FIG. 12 and with continuing reference to FIGS. 11a and 11b, a circuit for use with the second embodiment RF tag 16 includes a transceiver 139 for exciting RF tag 16 with an excitation signal and for detecting the response of RF tag 16 to the excitation signal. More specifically, transceiver 139 includes a transmitter 144 that outputs a magnetic excitation signal 140 via a transmit antenna 142. In response to receiving magnetic excitation signal 140, magnetostrictive element 132 commences oscillating at its resonant frequency thereby generating an RF response signal 146 which is received by a receive antenna 148 and processed by a receiver 150. When exposed to discharged fluid, however, liquid absorbent material 138 expands into contact with magnetostrictive element 132, as shown by dashed line 156 in FIG. 11b. This contact inhibits the vibration of magnetostrictive element 132 in response to magnetic excitation signal 140 whereupon the amplitude and/or the frequency of RF response signal 146 changes.

To facilitate the absorption of discharged fluid by liquid absorbent material 138, housing 130 includes one or more apertures 158 which enable discharged fluid to enter cavity 76 whereupon it is absorbed by liquid absorbent material 138. Alternatively, apertures 158 can be omitted and a wicking element (not shown) can be connected between the outside of housing 130 and liquid absorbent material 138 for wicking discharged fluid into liquid absorbent material 138. Still further, apertures 158 and liquid absorbent material 138 can be omitted and all or part of housing 130 can be made of material that swells or weakens and collapses in the presence of discharged fluid, thereby mechanically damping the response of magnetostrictive element 132 to magnetic excitation signal 140. In response to detecting a change in the amplitude and/or frequency of RF response signal 146, detector 58 activates alarm 60.

The second embodiment RF tag 16 shown in FIGS. 11a and 11b is strictly for the purpose of illustration and is not to be construed as limiting the invention. An nonlimiting example of the second embodiment RF tag 16 is disclosed in U.S. Pat. No. 6,182,352 to Deschenes et al.

Figure 13:
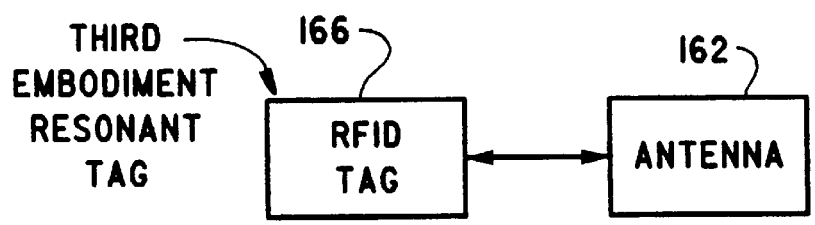
FIG. 13 is a top view of a third embodiment resonant tag which can be excited with an excitation signal output by one of the circuits shown in FIGS. 6–10 and the response of which can be detected thereby.

With reference to FIG. 13, a third embodiment RF tag 16 includes an antenna 162 coupled to a radio frequency identification (RFID) tag 166. RFID tag 166 can be any one of the RFID tags of the type know in the art of EAS that operate in the energy absorption mode or the energy radiation mode. Each prior art RFID tag that operates in the energy absorption mode absorbs energy from the excitation signal used to stimulate the RFID tag in one or more unique frequencies or unique bands of frequencies that can be detected by detector 58. Each prior art RFID tag that operates in the energy radiation mode outputs a unique wireless response signal in response to receiving the excitation signal. Each unique wireless response signal can include, without limitation, one or more frequencies or band of frequencies that can be detected by detector 58. Each wireless response signal output by a prior art energy radiation mode RFID tag may comprise one or more frequencies included in the excitation signal, one or more frequencies not included in the excitation signal or some combination thereof.

The third embodiment RF tag 16 shown in FIG. 13 is strictly for the purpose of illustration and is not to be constructed as limiting the invention. One, nonlimiting example of a third embodiment RF tag 16 is disclosed in U.S. Pat. No. 5,963,134 to Bowers et al.

The foregoing description of the general operation of the various embodiments of RF tag 16 are included herein for the purpose of illustration and are not to be construed as limiting the invention. To this end, the excitation signal used to stimulate each of the foregoing embodiments of RF tags 16 can be one that is swept from a starting frequency to an ending frequency, a broadband excitation signal or a narrowband excitation signal depending on, among other things, the stimulation requirement of the specific embodiment RF tag 16 being utilized and/or the configuration of the remote excitation and detection circuitry utilized therewith. Hence, the foregoing descriptions of excitation signals used to stimulate the various embodiments of RF tags 16 are strictly for the purpose of illustration and are not to be construed as limiting the invention. Moreover, the circuitry shown in FIGS. 6–10 and 12 are strictly for the purpose of illustration and are not to be construed as limiting the invention.

With reference back to FIGS. 1a, 1b, 2a, 2b, 4a and 4b, use of the various embodiments of RF tag 16 in accordance with the present invention will now be described. In use, diaper 2 or pad 4 is positioned to receive fluid discharged from a patient. In the absence of fluid discharged from the patient, absorbent material 14 or 20 is dry. Under this circumstance, when the first embodiment RF tag 16 operating in the energy absorption mode receives the excitation signal, it selectively absorbs energy from the excitation signal at its resonant frequency. This absorption produces in the excitation signal a unique change that can be detected by detector 58.

However, when the patient discharges fluid into diaper 2 or pad 4, the discharged fluid is absorbed by liquid absorbent material 14 or 20. When the discharged fluid absorbed by liquid absorbent material 14 or 20 contacts inductor L1 or L2 or capacitor C1 or C2, electrolytes contained in this discharged fluid create low resistance paths which detune the first embodiment RF tag 16 thereby changing its resonant frequency. In response to this change, the frequency where energy in the excitation signal is absorbed by the first embodiment RF tag 16 changes. In response to detecting this change in the frequency where energy is absorbed in the excitation signal, detector 58 activates alarm 60.

Since electrolytes contained in the discharged fluid render the discharged fluid conductive, discharged fluid covering all or part of one or both surfaces of RF tag 16 also acts as a shield that attenuates or blocks receipt of excitation signal by inductor L1 or L2 or capacitor C1 or C2. Hence, detector 58 can also or alternatively be configured to detect a change, i.e., a reduction, in the absorption of energy by the first embodiment RF tag 16 due to discharged fluid covering all or part of on one or both surfaces thereof. If sufficient discharged fluid covers one or both surfaces of the first embodiment RF tag 16, the absorption of the excitation signal detected by detector 58 can decrease to zero or null.

To avoid the possibility that discharged fluid may not contain sufficient electrolytes to detune first embodiment RF tag 16 or shield circuit elements L1, L2, C1 or C2 from the excitation signal, a dry or powdered electrolyte, such as salt, can be embedded in absorbent material 14 or 20 or in a wetable membrane 46 covering one or both surfaces of the first embodiment RF tag 16. When discharged fluid contacts this dry or powdered electrolyte, the dry or powdered electrolyte dissolves forming a concentrated electrolyte solution that modifies the resonant frequency of first embodiment RF tag 16 and/or shields circuit elements L1, L2, C1 and/or C2 from the excitation signal.

The use of wetable membrane 46 on one or both surfaces of the first embodiment RF tag 16 engenders detuning and/or shielding of circuit elements L1, L2, C1 and/or C2 of first embodiment RF tag 16 when discharged fluid is present. However, wetable membrane 46 can be replaced by a fluid impermeable coating 48 on one or both surfaces of the first embodiment RF tag 16 for maintaining one or both surfaces in spaced relation to discharged fluid received in absorbent material 14 or 20. The use of coating 48 on one or both surfaces of the first embodiment RF tag 16 engenders shielding circuit elements L1, L2, C1 and/or C2 from receiving the excitation signal.

In the energy radiation mode of operation, where a wireless response signal output by the first embodiment RF tag 16 after termination of the excitation signal is utilized to detect the absence or presence of discharged fluid, detector 58 is configured to detect a change in the resonant frequency of the wireless response signal due to discharged fluid detuning circuit element L1, L2 C1 and/or C2 and/or a change, i.e., a reduction, in the signal strength, e.g., amplitude, of the wireless response signal due to discharged fluid shielding circuit element L1, L2, C1 and/or C2 from the excitation signal. In response to detecting one or both of these changes, detector 58 activates alarm 60.

In accordance with the present invention, the third embodiment RF tag 16 shown in FIG. 13 can be utilized in the energy absorption mode of operation where, in response to receiving an excitation signal in the absence of discharged fluid on or adjacent the third embodiment RF tag 16, RFID tag 166 selectively absorbs energy at one or more unique frequencies and/or bands of frequencies of the excitation signal. However, when discharged fluid is present, it attenuates the excitation signal received by the third embodiment RF tag 16 whereupon the selective absorption by RFID tag 166 of energy at one or more unique frequencies and/or bands of frequencies of the excitation signal is reduced. In response to detecting a suitable reduction in the absorbed energy at one or more frequencies and/or bands of frequencies of the excitation signal, detector 58 activates alarm 60. This reduction in absorbed energy at each of one or more unique frequencies or bands of frequencies of the excitation signal can occur to the point where said absorption is zero or null.

The third embodiment RF tag 16 can also be used in the energy radiation mode of operation where, in response to absorbing energy from the excitation signal via antenna 162 in the absence of discharged fluid on or adjacent the third embodiment RF tag 16, RFID tag 166 outputs via antenna 162 a unique wireless response signal comprised of one or more frequencies or bands of frequencies. However, when discharged fluid is present, it attenuates the excitation signal received by the third embodiment RF tag 16 and/or the unique wireless response signal output by RFID tag 166 whereupon an amplitude of one or more frequencies or bands of frequencies of the unique wireless response signal is reduced. In response to detecting a suitable reduction in the amplitude of one or more frequencies or bands of frequencies of the unique wireless response signal, detector 58 activates alarm 60. This reduction in the amplitude of one or more frequencies or bands of frequencies can occur to the point where said amplitude is zero or null.

With reference back to FIGS. 11a, 11b and 12, in accordance with the present invention, the second embodiment RF tag 16 is utilized exclusively in the energy radiation mode of operation. In this mode of operation, when detector 58 detects a change in the amplitude or frequency of RF response signal 146 due to the presence of discharged fluid, detector 58 activates alarm 60. Absent a change in the amplitude or frequency of RF response signal 146, detector 152 takes no action.

As discussed above, the various embodiments of RF tag 16 can be utilized to detect the absence and presence of discharged fluid. To avoid premature or early detection of the presence of discharged fluid when diaper 2 or pad 4 does not need to be changed immediately, one of the various embodiments of RF tag 16 can be positioned at a suitable location in diaper 2 or pad 4 so that liquid absorbent material 14 and 20 absorbs a minimum volume of discharged fluid before the actual or detected operation of RF tag 16 is affected. Moreover, as shown in FIG. 1, diaper 2 can include two or more RF tags 16 and 16', each having a different unique response to an excitation signal, positioned at different locations in diaper 2. These two or more RF tags 16, 16' can be utilized to detect the remaining capacity of diaper 2, especially liquid absorbent material 14, to absorb discharged fluid. For example, a plurality of RF tags 16, 16' can be positioned increasingly distant from the discharge orifice(s) of the patient wearing diaper 2. As discharged fluid covers or comes into contact with each RF tag 16, 16', its unique response varies in one of the manners described above. When the first RF tag 16 of the plurality is covered, its unique response changes whereas the unique response of the other RF tags, e.g., 16' is unaffected. This indicates that diaper 2 is partially full.

When the discharged fluid covers or comes into contact with the RF tag, e.g., 16,' furthest away from the discharge orifice(s) of the patient, its unique response changes whereupon it can be determined that diaper 2 is nearing or has reached its capacity to absorb discharged fluid. The changing of the unique response of each of a plurality of RF tags 16, 16' can be utilized as a basis for determining the urgency with which diaper 2 must be changed based on the remaining capacity of diaper 2 to store discharged fluid. In a similar manner, pad 4 can include two or more RF tags 16, 16' for determining when pad 4 is reaching its capacity to store discharged fluid.

It is envisioned that under certain circumstances where the change in energy absorbed by RF tag 16 and/or the change in a response signal output by RF tag 16 is utilized as the basis for determining the presence of discharged fluid, it may be desirable to also provide a means for detecting that the patient is adjacent the transceiver that excites and detects the response of RF tag 16. This is especially desirable for remote detection of the absence or presence of discharged fluid where the transceiver is positioned to detect an RF tag 16 associated with a patient lying on a bed or sitting in a wheelchair. To this end, diaper 2 and/or pad 4 can include a second RF tag 16', having a different unique response than RF tag 16, positioned where it will not be exposed to discharged fluid. Thus, while RF tag 16 can be utilized to detect for the presence or absence of discharged fluid, RF tag 16' is utilized to detect for the presence or absence of the patient adjacent the transceiver. In the case where no response to the excitation signal is received from RF tag 16 and RF tag 16', it is assumed that the patient is not within the range of the transceiver. In contrast, when no response to the excitation signal is received from RF tag 16 but a response is received from RF tag 16', it can be assumed that RF tag 16 is operating in the presence of discharged fluid.

Two RF tags 16 can be located in diaper 2 to emphasize the detection of urine discharge and moist fecal discharge. To this end, diaper 2 can be configured whereupon absorbent material 14 causes discharged urine to move laterally away from its entry point into diaper 2. Accordingly, to avoid premature detection of the presence of discharged fluid, one RF tag 16 can be positioned at a location in diaper 2 to delay the detection of discharged urine. In contrast, it is desired that a second RF tag 16 be located in diaper 2 to quickly detect for the presence of moist fecal discharge.

More specifically, two or more RF tags 16 can be located in diaper 2 to differentially detect if it is dry, if just urine is present, and/or if moist fecal discharge is present. Modem diapers are arranged to quickly wick urine away from the skin surrounding the body's urine discharge orifice and to stabilize it in deep layers of the diaper. However, fecal discharge is trapped next to the patient's skin. When wet with urine, fecal enzymes may be re-activated to irritate or even digest adjacent skin. Therefore, not all wet diapers need to be immediately changed since, depending on the quantity of urine discharged, they can be constructed to contain several urine discharges before reaching their fluid holding capacity. In contrast, it is almost always important to rapidly change a diaper soiled with fecal discharge.

Accordingly, one or more uniquely identifiable RF tags 16 can be located within deep moisture retaining structures of diaper 2 for detecting the presence of discharged fluid and/or when diaper 2 is reaching its fluid retaining capacity. Still further, one or more other uniquely identifiable RF tags 16, especially those coated with a dry electrolyte containing wetable membrane 46, can be located in diaper 2 adjacent the patient's fecal discharge orifice for detecting the presence of fecal discharge. Preferential response to fecal discharge can be enhanced by placing a moisture resistant barrier under the RF tag 16 near the patient's fecal discharge orifice to avoid discharged urine received in diaper 2 from affecting its response. This moisture barrier avoids discharged urine from spreading to the RF tag 16 near the fecal discharge orifice thereby making it more likely that this RF tag 16 will respond to moist fecal discharge.

Detector 58 can be programmed to detect the response of these RF tags 16 to one or more excitation signals and to activate alarm 60 when diaper 2 is full with urine and/or when it is likely that diaper 2 has been soiled with fecal discharge.

Referring back to FIGS. 4a, 4b and 5, to avoid patient discomfort when wearing diaper 2 or lying on pad 4, the first embodiment RF tag 16 preferably comprises flexible substrate 32 that flexes in response to interaction with the patient. In the simplest case where RF tag 16 includes of only one inductor L and one capacitor C, and is resonant at only one frequency, flexing RF tag 16 causes a change in the inductance of inductor L whereupon the resonant frequency of such first embodiment RF tag 16 would change thereby adversely affecting the detection of RF tag 16 which has not yet been exposed to discharged fluid. To avoid this problem, the first embodiment RF tag 16 preferably includes a single circuit having two or more inductors and two or more capacitors, resulting in a circuit having two or more distinct resonant frequencies, with a predetermined frequency difference therebetween, formed on flexible substrate 32. For example, the first embodiment RF tag 16 shown in FIGS. 4a and 4b includes a first inductor circuit element formed by conductive path 30, in parallel with conductive areas 42 and 44, i.e., capacitor C1. Further, the series connected circuit elements L2, formed by conductive path 30, and C2, formed by conductive areas 34 and 46, are themselves additionally connected in parallel with L1 and C1, forming the equivalent circuit shown in FIG. 5. Since inductors L1 and L2 are generally coaxial and coplanar with each other, when the first embodiment RF tag 16 is subject to flexing, the inductances of inductors L1 and L2 change substantially by the same amount whereupon the first resonant frequency, determined substantially by L1, changes by the same amount as the second resonant frequency, determined substantially by L2, and so the frequency difference therebetween remains constant.

Figure 14:
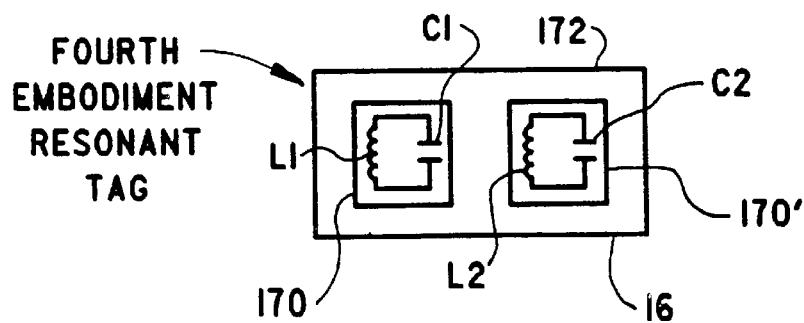
FIG. 14 is a schematic drawing of a fourth embodiment resonant tag.

The frequency difference of the first embodiment RF tag 16 can be utilized to identify a particular RF tag 16 in a group of RF tags 16 where each one has a unique frequency difference. In the absence of discharged fluid, the first and second resonant frequencies of the first embodiment RF tags 16 each have a first amplitude in response to an excitation signal. However, when discharged fluid is present in diaper 2 or pad 4, the first and second resonant frequencies of the first embodiment RF tags 16 each have a second, reduced amplitude response to the excitation signal. This difference in amplitude can be utilized in the energy absorption mode of operation and/or in the energy radiation mode of operation for detecting the absence or presence of discharged fluid. Moreover, as shown in FIG. 14, a fourth embodiment RF tag 16 having resonant circuits 170 and 170', each having a different response to an excitation signal, spaced from each other on a flexible insulating substrate 172 can be utilized in place of the first embodiment RF tag 16, albeit with less control of the mutual change in the inductance's of inductors L1 and L2 when substrate 172 is flexed.

As can be seen, the combination of diaper 2 or pad 4, liquid absorbent material 14 or 20 and one or more RF tags 16 enables remote detection of the absence and presence of discharged fluid without having to physically inspect diaper 2 or pad 4. This is particularly useful in hospital and/or nursing home environments where physical inspection may unnecessarily disrupt the patient when diaper 2 or pad 4 does not need to be changed. Moreover, while pad 4 has been described in connection with an incontinence pad, pad 4 can also take the form of a bandage or other type of gauze or pad configured for application to bleeding or oozing wounds of a patient.

In addition to their use in the third embodiment RF tag 16 described above, prior art RFID tags 166 that produce patterns of unique frequencies or bands of frequencies in either the energy absorption mode or energy radiation mode of operation can also be utilized for patient identification. Specifically, some prior art RFID tags can absorb energy from plural, e.g., up to 64, unique frequencies or bands of frequencies of an excitation signal or can output a response signal having plural, e.g., up to 64, unique frequencies or bands of frequencies. In use, these prior art RFID tags are affixed to diapers 2 and/or pads 4. Each patient in a particular location, e.g., a nursing home, is then associated with pattern of frequencies or bands of frequencies produced by RFID tags 166 that is unique from the pattern of frequencies or bands of frequencies associated with other patients. Each patient would then only used diapers 2 or pads 4 having RFID tags 166 including the unique pattern of frequencies or bands of frequencies assigned to that patient. A suitable excitation signal can then be utilized to stimulate one or more third embodiment RF tags 16, each including an RFID tag 166 that produces a pattern of frequencies or bands of frequencies that is unique to a particular patient. From the response to this excitation signal, the location and/or identity of one or more of the patients can be determined.

With reference back to FIGS. 1a, 1b, 3a and 3b, use can be made of two or more RF tags 16 for positioning monitoring of a patient. This use of two or more RF tags 16 is particularly useful for bedridden or wheelchair confined patients for prevention of pressure ulcers, also known as bedsores. In connection with position monitoring, two or more RF tags 16, e.g., RF tags 16A, 16B and 16C can be affixed to underwear 6 or disposable diaper 2. Each RF tag 16A–16C produces a unique response to an excitation signal that can be detected independent of the response of the other RF tags to the excitation signal. RF tags 16A–16C can be affixed on or adjacent a waistband 180 of underwear 6 or waistband 178 of diaper 2, with RF tag 16A positioned adjacent the patient's left hip, RF tag 16B positioned adjacent the patient's right hip and RF tag 16C positioned adjacent the patient's lower back.

Figure 15:
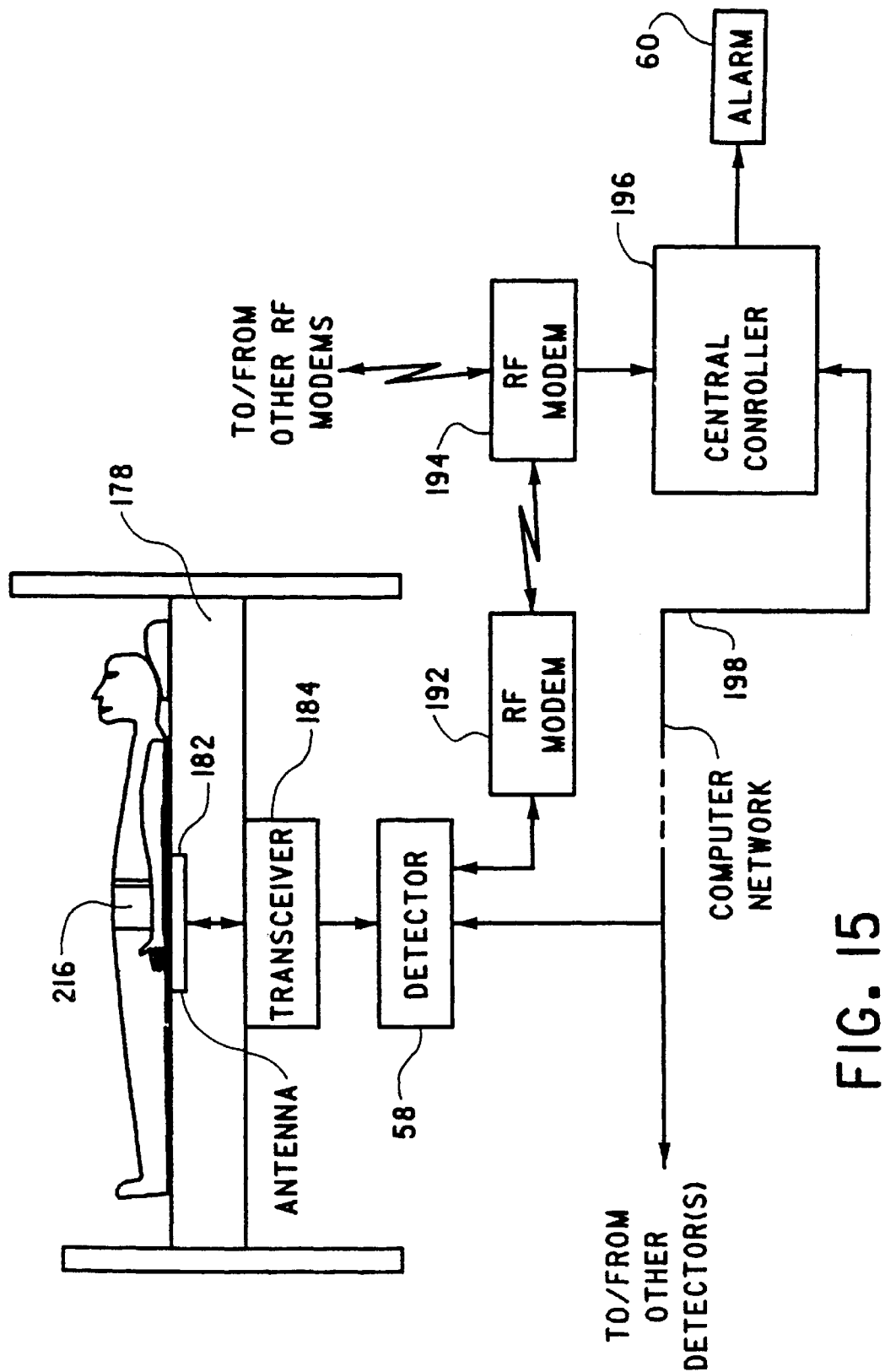
FIG. 15 is a schematic illustration of a supine patient wearing the diaper shown in FIGS. 1a and 1b or the undergarment shown in FIGS. 3a and 3b having a circuit for exciting the resonant tags thereof with an excitation signal and for detecting the response of the resonant tags to the excitation signal.

With reference to FIG. 15 and with continuing reference to FIGS. 1a, 1b, 3a and 3b, when a patient wearing diaper 2 or underwear 6 having RF tags 16A–16C affixed thereto lies supine on a mattress 178, RF tag 16C will most strongly interact with an antenna 182 which is positioned on or adjacent a surface of mattress 178.

In use, a transceiver 184 excites RF tags 16A–16C with an excitation signal via antenna 182 and detects the unique response of each RF tag 16A–16C to said excitation signal. Detector 58 determines from the detected response of each RF tag 16A–16C, especially the amplitude of the unique energy absorption of the excitation signal caused by each RF tag 16A–16C or from the amplitude of the unique wireless response signal output by each RF tag 16A–16C, which RF tag 16A–16C is closet to antenna 182. For example, when the patient is on his right side, RF tag 16B is closet to the surface of mattress 178 and will return to antenna 182 the strongest response to the excitation signal. Similarly, when the patient is on his left side, RF tag 16A is closet to the surface of mattress 178 and will return to antenna 182 the strongest response to the excitation signal. In general, the strongest response to the excitation signal detected by antenna 182 is received from the RF tag 16A–16C that is closet to antenna 182.

Figure 16:
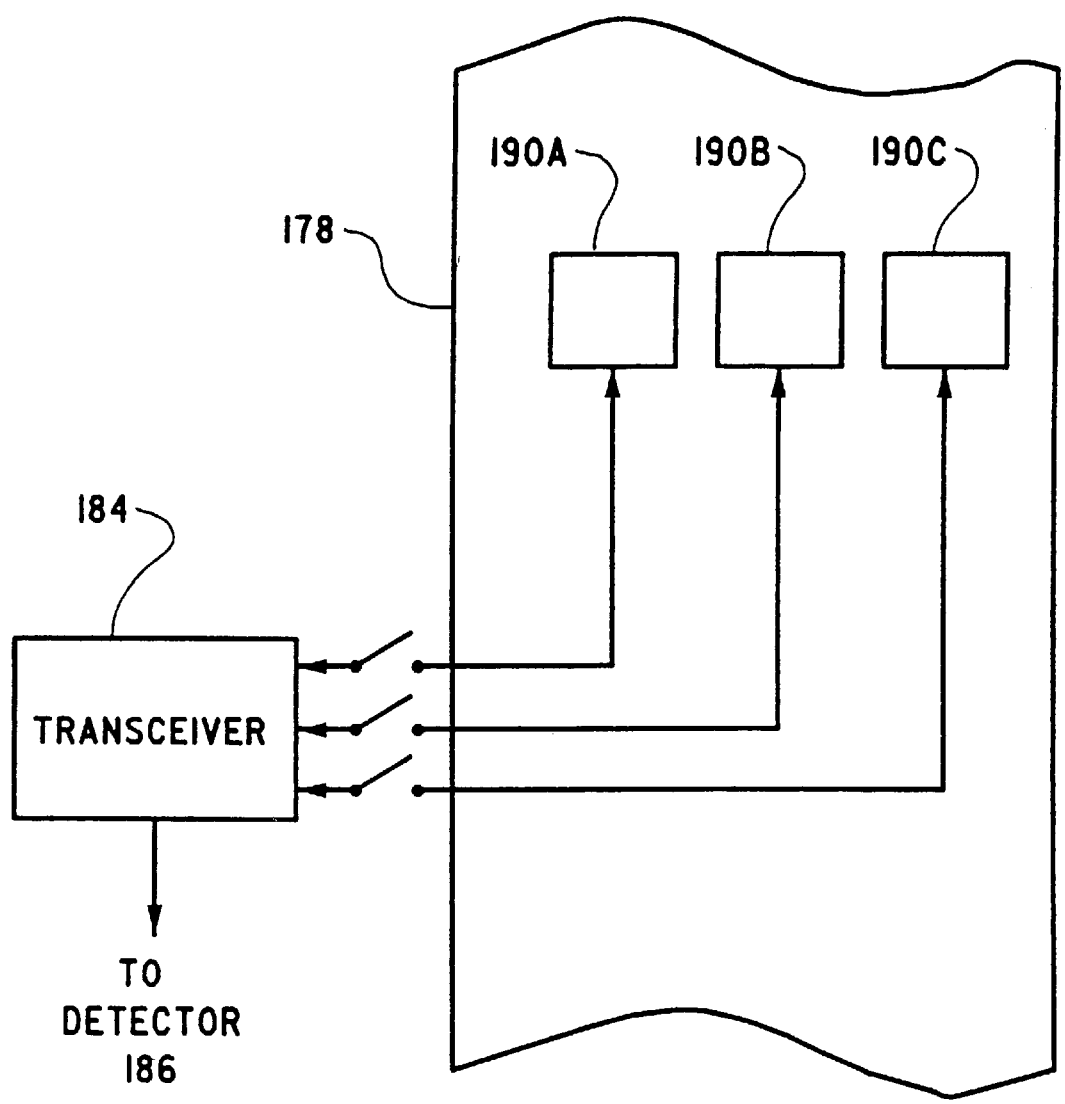
FIG. 16 is an isolated view of the mattress shown in FIG. 15 including a plurality of antennas supported thereby.

With reference to FIG. 16 and with continuing reference to FIG. 15, mattress 178 can include one large antenna 182 or a plurality of small antenna 190A–190C selectively, individually connectable to transceiver 184. In operation, each antenna 190A–190C is selectively connected to transceiver 184 which causes each antenna 190A–190C to output an excitation signal and which detects the response of each RF tag 16A–16C responding to the excitation signal. By determining which antenna 190A–190C has the maximum response, the horizontal location of the patient on mattress 178 can be determined. Moreover, from either the unique energy absorption of the excitation signal caused by each RF tag 16A–16C or from the unique response signal output by each RF tag 16A–16C, the orientation of the patient wearing diaper 2 or underwear 6 can be determined.

When the response of two or more antenna 190A–190C indicate that two RF tags 16A–16C are equally near said antennas, but no RF tag 16A–16C is coupled to the maximum amount possible, it can be concluded that the patient wearing diaper 2 or underwear 6 is oriented between the three positions where an RF tag 16A–16C is parallel to one of antennas 190A–190C. Moreover, if no antenna 190A–190C detects the response of RF tag 16C, but responses are detected from RF tags 16A and 16B, it can be concluded that the patient wearing diaper 2 or underwear 4 is lying prone facedown. This may be considered a dangerous position for a movement impaired patient on a soft mattress 178. Moreover, if no response is detected from RF tag 16A, but sub-maximum responses are detected from RF tag 16B and 16C, it can be concluded that the patient wearing diaper 2 or underwear 6 is oriented about halfway between supine and his right side.

With reference back to FIG. 15, detector 58 can be coupled to an RF modem 192 for wirelessly communicating data regarding the incontinence status of the patient and/or data regarding the position of the patient to a central controller 196 via an RF modem 194 coupled thereto. Other RF modems (not shown) can also communicate like data to central controller 196 via RF modem 194. Alternatively, detector 58 and one or more other detectors (not shown) can be communicatively connected to central controller 196 via a computer network 198. Regardless of the manner in which central controller 196 receives data regarding the incontinence status or position status of a particular patient, central controller 196 can evaluate this data and activate alarm 60 when a diaper 2 or pad 4 of a particular patient needs to be changed and/or when the position of a particular patient requires changing to avoid pressure ulcers.

Detector 58 and/or central controller 196 can be programmed as desired to store for each patient the response of each RF tag 16 to one or more excitation signals. From this data, a change in the incontinence status and/or position of a particular patient can be determined. For example, data regarding the response of each RF tag 16 in one or both of energy absorption mode and/or energy radiation mode of operation, in the absence of discharged fluid can be stored for future comparison with the response of RF tag 16 when discharged fluid is present. Similarly, each change or lack of change in the position of a patient determined from the strength of energy absorption and/or energy radiation from a plurality of RF tags 16 can be stored. This data can then be analyzed by detector 58 and/or center controller 196 in a manner known in the art to determine the absence or presence of discharged fluid and/or whether the patient is changing positions sufficiently often to avoid pressure ulcers.

As can be seen, the present invention enables remote incontinence and position monitoring quickly and efficiently. It enables accurate determination of the need to change a diaper 2 or pad 4 and/or of the need to reposition a patient to avoid pressure ulcers.

The present invention has been described with reference to the preferred embodiments. Obvious modifications and alterations will occur to others upon reading and understanding the preceding detailed description. For example, when used for position monitoring, any article which can be worn or affixed to a patient whereupon the RF tags 16 thereof are positioned on or adjacent known points of the patients anatomy can be utilized. Moreover, one or more of these RF tags 16 can be disposed in diaper 2 or underwear 6 at locations other than waistband 178 or 180. In addition, RF tags 16 included in diaper 2 and/or underwear 6 used for position monitoring can also be used to detect for the presence or absence of discharged fluid. It is intended that the invention be construed as including all such modifications and alterations insofar as the come within the scope of the appended claims or the equivalents thereof.

The invention claimed is:

1. A patient position monitoring system comprising:
   a plurality of RF tags, each RF tag responsive to at least one wireless excitation signal for at least one of causing a unique change in the excitation signal and outputting a unique wireless response signal;
   an article configured to be worn by a patient, the article having the plurality of RF tags received at predetermined locations thereon, the article configured to avoid movement of each RF tag relative to a body of the patient when it is being worn; and
   a transceiver for (i) supplying a first excitation signal, for detecting for each RF tag responding to the first excitation signal at least one of a strength of the unique change in the first excitation signal and a strength of the unique response signal and for determining therefrom a first relative position of each responding RF tag with respect to each other, and for (ii) supplying a second excitation signal, for detecting for each RF tag responding to the second excitation signal at least one of a strength of the unique change in the second excitation signal and a strength of the unique response signal and for determining therefrom a second relative position of each responding RF tag with respect to each other.

2. The system as set forth in claim 1, further including a detector responsive to at least one of:
   a change in the first and second relative positions of one or more responding RF tags for generating an indication related to a change in position of the patient between the first and second excitation signals; and
   a lack of change in the first and second relative positions of one or more responding RF tags for generating an indication related to an absence of a change in position of the patient between the first and second excitation signals.

3. The system as set forth in claim 1, wherein the transceiver includes at least one antenna positioned adjacent a patient receiving surface for transmitting excitation signals and the system further includes a detector responsive to interaction between the at least one antenna and each RF tag responding to each excitation signal for detecting the strength of the unique change in the excitation signal caused by each RF tag.

4. The system as set forth in claim 3, wherein the patient receiving surface is one of a surface of mattress and a surface of a chair.

5. The system as set forth in claim 1, wherein the transceiver includes at least one antenna positioned adjacent a patient receiving surface for transmitting excitation signals and for receiving after each excitation signal is terminated the unique response signal output by each RF tag responding thereto, and the system further includes a detector coupled to the a least one antenna for detecting the strength of each unique response signal received thereby.

6. The system as set forth in claim 1, wherein the transceiver includes at least one first antenna positioned adjacent a patient receiving surface for transmitting each excitation signal and the system further includes a detector responsive to interaction between a least one second antenna and each RF tag responding to each excitation signal during transmission thereof for detecting the strength of the unique change in the excitation signal caused by each RF tag.

7. The system as set forth in claim 1, wherein the transceiver includes a plurality of antennas each positioned at a unique location adjacent a patient receiving surface, with each antenna individually selectable for transmitting at least one excitation signal, and the system further includes a detector responsive to each antenna for detecting the unique change in the excitation signal caused by each RF tag responding to the excitation signal.

8. A patient position monitoring method comprising the steps of:
   (a) providing an article configured to be worn by a patient, the article having affixed thereto a plurality of RF tags, each RE tag responsive to a wireless excitation signal for at least one of causing a unique change in the excitation signal and outputting a unique wireless response signal;

(b) stimulating the RF tags with a first wireless excitation signal when the article is being worn by a patient;

(c) detecting for each RF tag responding to the first excitation signal, at least one of the unique change in the excitation signal and the unique response signal;

(d) determining for each RF tag responding to the first excitation signal a signal strength of the at least one unique change in the excitation signal and the unique response signal; and (e) determining from the signal strengths determined in step (d), relative locations of the RF tags responding to the first excitation signal with respect to each other.

9. The method as set forth in claim 8, further including the steps of:

(f) stimulating the RF tags with a second wireless excitation signal;

(g) detecting for each RF tag responding to the second excitation signal, at least one of the unique change in the excitation signal and the unique response signal;

(h) determining for each RF tag responding to the second excitation signal a signal strength of the at least one unique change in the excitation signal and the unique response signal; and determining from the signal strengths determined in step (h), relative locations of the RF tags responding to the second excitation signal with respect to each other.

10. The method as set forth in claim 9, wherein:

the unique change in the excitation signal includes energy absorption in one or more frequencies of the excitation signal; and the unique response signal of each RF tag includes a unique frequency.

11. A patient orientation monitoring system comprising:

an article configured to be worn by a patient;

a plurality of RF tags supported by the article, each RF tag responsive to a wireless excitation signal for at least one of causing a unique change in the excitation signal and outputting a unique wireless response signal; and means for outputting a first wireless excitation signal when the article is being worn by the patient and for receiving from each RF tag responding to the first excitation signal at least one of the unique change in the excitation signal and the unique response signal and means for determining therefrom first relative positions of the responding RF tags with respect to each other.

12. The system as set forth in claim 11, wherein the determining means includes a detector programmed to determine from tile first relative positions of the responding RF tags with respect to each other all orientation of the patient.

13. The system as set forth in claim 11, wherein the means for outputting and receiving outputs a second wireless excitation signal and receives from each RF tag responding to the second excitation signal at least one of the unique change in the excitation signal and the unique response signal, and the determining means determines therefrom second relative positions of the responding RF tags with respect to each other.

14. The system as set forth in claim 13, wherein the determining means includes a detector programmed to determine from the first and second relative positions of the responding RF tags with respect to each other whether the patient has changed orientation.

15. The system as set forth in claim 11, wherein the means for outputting and receiving includes an antenna positioned adjacent a patient receiving surface for transmitting each excitation signal and for receiving from each RF tag responding to the excitation signal the at least one of unique change in the excitation signal and the unique response signal, and the determining means includes a detector responsive to the antenna for detecting for each RF tag responding to the excitation signal the at least one of the unique change in the excitation signal and the unique response signal.

16. The system as set forth in claim 15, wherein the patient receiving surface is one of a surface of mattress and a surface of a chair.

17. The system as set forth in claim 11, wherein the means for outputting and receiving include a plurality of antennas positioned at a different location adjacent a patient receiving surface, each antenna individually selectable for transmitting each excitation signal, and the determining means includes a detector response to each antenna for detecting for each RF tag responding to the excitation signal the at least one of the unique change in the excitation signal and the unique wireless response signal.

* * * * *